United States Patent [19]

Berber et al.

[11] 4,206,650

[45] Jun. 10, 1980

[54] DEVICE FOR INTRODUCING SAMPLES INTO FLUID ANALYZER

[76] Inventors: Viktor A. Berber, ulitsa Shelkovichnaya, 184, kv. 65; Evgeny S. Pervushin, ulitsa Shelkovichnaya, 182, kv. 71; Marat N. Jushunev, ulitsa Shelkovichnaya, 184-a, kv. 22; Ernest M. Garanin, ulitsa 20 let VLKSM, 100, kv. 17; Vladimir G. Kholin, ulitsa Shelkovichnaya, 194, kv. 30; Khafiz M. Murtazin, 6 Internatsionalny proezd, 20, all of Saratov, U.S.S.R.

[21] Appl. No.: 935,503

[22] Filed: Aug. 21, 1978

[51] Int. Cl.$^2$ .................. G01N 1/20; G01N 21/00
[52] U.S. Cl. .................. 73/421 R; 55/274; 73/61.1 R; 356/36
[58] Field of Search ............. 73/61 R, 61.4, 421 R; 356/36

[56] References Cited

U.S. PATENT DOCUMENTS

| | | | |
|---|---|---|---|
| 2,163,000 | 6/1939 | Goodhue et al. | 73/61.4 |
| 3,334,516 | 8/1967 | Cedrone | 73/61 R |
| 3,669,542 | 10/1969 | Capellaro | 356/36 |
| 3,669,542 | 6/1972 | Capellaro | 356/36 |
| 3,869,903 | 3/1975 | Beach et al. | 73/61.4 |
| 3,947,251 | 3/1976 | Quame | 73/421 R |

FOREIGN PATENT DOCUMENTS 217686  5/1968  U.S.S.R. .................. 73/61.4

Primary Examiner—Daniel M. Yasich
Attorney, Agent, or Firm—Fleit & Jacobson

[57] ABSTRACT

According to the invention, the device for introducing samples into an analyzer of an apparatus for granulometric analysis of particles contained in fluids comprises a funnel whose outlet is connected to a channel communicating with a supply channel of an analyzer. Immediately downstream of the funnel, the channel has a horizontal portion of a length roughly equal to 3 to 5 channel diameters. Downstream of the horizontal portion there is a vertical portion whose diameter first gradually increases until it is 4 to 6 times greater than its initial value and is then gradually reduced to the initial value.

5 Claims, 1 Drawing Figure

DEVICE FOR INTRODUCING SAMPLES INTO FLUID ANALYZER

FIELD OF THE INVENTION

The present invention relates to measuring equipment and, more particularly, to a device for introducing samples into an analyzer of an apparatus for granulometric analysis of particles contained in fluids. The invention is readily applicable to the analysis of suspensions of low concentrations. It is applicable, for example, to systems for the analysis of particles of impurities contained in fuels and oils.

BACKGROUND OF THE INVENTION

There is known a device for introducing samples into an analyzer of an apparatus for granulometric analysis of particles contained in fluids, comprising a vertical cone-shaped funnel and a straight vertical channel which communicates the outlet of the funnel with a supply channel of an analyzer.

A sample of a fluid to be subjected to analysis is poured into the funnel and flows through the vertical channel to the supply channel of the analyzer where particles of impurities are analyzed.

The pouring of fluid into the funnel is usually accompanied by the formation of air bubbles which may reach the analyzer with the flow of fluid and be mistaken for particles of impurities.

The result is a reduced accuracy of the analysis because the number of particles detected by the apparatus is greater than their actual quantity. To eliminate the air bubbles, the sample must either be evacuated or allowed to settle so that the air bubbles should be driven out by the buoyancy forces; in the latter case it is necessary to close the discharge cock. The settling time is dependent on the size of the bubbles, as well as on the viscosity and density of the fluid. However, as air bubbles are removed in the course of settling, particles of impurities precipitate under gravity. Some of these particles precipitate on the walls of the funnel, whereas others reach the vertical channel and get as far as the supply channel of the analyzer. If a stopcock is installed at the analyzer's inlet, particles precipitate on the submerged part of the stopcock; when the latter is opened these are washed away by the flow and carried to the analyzer for the most part in the form of large aggregates. As a result, the apparatus detects particles in a number smaller than that contained in the sample, and of a size greater than that of particles originally contained in the sample. Besides, the friction parts of stopcocks, as a rule, also produce impurities, which accounts for considerable errors in determining the amount of impurities contained in fluids.

The latter disadvantage is eliminated by installing and closing a stopcock at the outlet of the analyzer. However, in such a case some of the precipitated particles pass through the analyzer which is out of operation, keeping in mind that it is designed to determine the amount and size of particles in a flow of fluid. As the analysis begins, the particles passed through the analyzer are not taken into account, wherefore the apparatus detects a lesser quantity of particles than that actually contained in the sample.

SUMMARY OF THE INVENTION

It is an object of the present invention to raise the accuracy of particle detection while analyzing individual samples of fluids and flows of fluids containing gas bubbles.

The foregoing and other objects of the invention are attained by providing a device for introducing samples into an analyzer of an apparatus for granulometric analysis of particles contained in fluids, comprising a funnel whose outlet is connected to a channel intended for communication with a supply channel of an analyzer, characterized, according to the invention, in that immediately downstream of the funnel the channel has a horizontal portion of a length roughly equal to 3 to 5 channel diameters, and in that downstream of the horizontal portion there is a vertical portion of a diameter which first gradually increases until it is 4 to 6 times greater than its initial value and is then gradually reduced to its initial value.

The device for introducing samples into an analyzer of an apparatus for granulometric analysis of particles contained in fluids according to the invention features an improved accuracy of analyzing particles contained in individual samples of fluids. The presence of the horizontal portion of the channel which communicates the funnel with the analyzer of the apparatus for granulometric analysis of particles contained in fluids makes it possible to allow a sample to settle during a period of time sufficiently long to remove air bubbles from the sample. Particles of impurities, which precipitate during the settling, are kept in the horizontal portion of the channel and then washed away and uniformly mixed with the fluid being analyzed in the expanded vertical portion of the channel. The manner in which a sample is introduced into the analyzer prevents detection of air bubbles and precipitation of particles during settling.

BRIEF DESCRIPTION OF THE ATTACHED DRAWING

Other objects and advantages of the present invention will become more apparent from the following detailed description of a preferred embodiment thereof to be read in conjunction with the accompanying drawing which is a schematic diagram of a device for introducing samples into an analyzer of an apparatus for granulometric analysis of particles contained in fluids, in accordance with the invention.

DETAILED DESCRIPTION OF THE INVENTION

Figure 1:
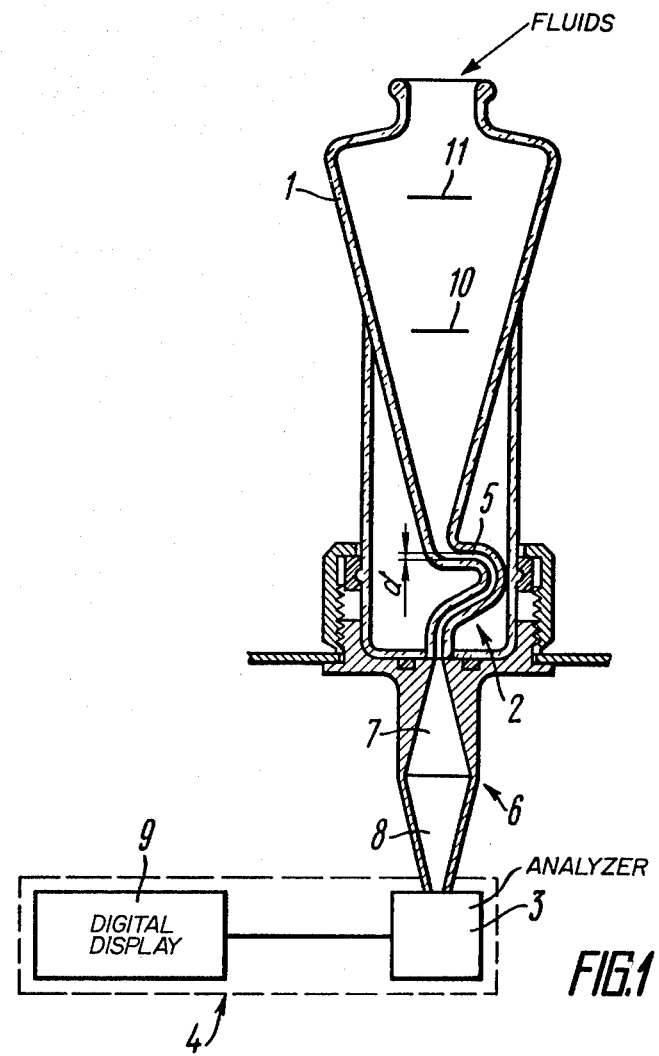

Referring to the attached drawing, the device for introducing samples into an analyzer of an apparatus for granulometric analysis of particles contained in fluids comprises a vertical cone funnel 1 having its outlet connected to a channel 2 intended for communication with a supply channel of an analyzer 3 of an apparatus 4 for granulometric analysis of particles contained in fluids. For instance, the outlet of channel 2 can be connected to the Sample Tube used with the particle sensor described in U.S. Pat. No. 3,669,542. This patent describes a sensing apparatus having an analyzer or sensor that detects light scattered by particles in liquid flowing between a light source and the sensor. Immediately downstream of the funnel 1, the channel 2 has a horizontal portion 5 of a length roughly equal to 3 to 5 diameters d of the channel 2. Downstream of the horizontal portion 5, the channel 2 has a vertical portion 6 of a diameter which is first gradually increased in a zone 7 until it is 4 to 6 times greater than its initial value and is then gradually reduced in a zone 8 to its initial value.

The apparatus 4 is provided with a digital display 9 indicating the amount and sizes of particles of impurities detected in fluids subjected to analysis.

It is expedient that the funnel 1 and the horizontal portion 5 of the channel 2 should be transparent to enable the analyst observe the disappearance of bubbles, as well as the precipitation and subsequent washing away of particles. The funnel 1 carries an upper mark 11 and a lower mark 10 indicating the volumes of samples.

The device for introducing samples into an analyzer of an apparatus for granulometric analysis of particles contained in fluids operates as follows.

Prior to analyzing a sample of a fluid, the analyzer 3, channel 2 and funnel 1 must be filled with a thoroughly purified fluid having a composition and properties similar to those of the fluid subjected to analysis. In the funnel 1, the fluid level must be as high as the mark 10. The fluid filling the analyzer 3, channel 2 and funnel 1 must be devoid of particles with sizes greater than the sensitivity threshold of the analyzer 3. This fluid must also be bubble-free.

A sample to be analyzed is poured into the funnel to fill it to the level of the mark 11 and is then allowed to settle to eliminate air bubbles produced by the pouring or sampling.

The settling time is dependent upon the viscosity and density of the fluid and the height of the fluid column. For example, a sample of 100 cm$^3$ of machine oil takes 1 or 2 minutes to settle.

The settling is accompanied by precipitation of particles of impurities suspended in the fluid. The larger and heavier particles accumulate in the horizontal portion 5 of the channel 2. As the fluid being analyzed is allowed to flow, these particles are washed away by the flow. To facilitate the washing away of such particles, the portion 5 is of a small diameter (3 to 4 mm). As the fluid being analyzed starts to flow, the apparatus 4 is brought into operation. As particles of impurities carried by the flow of fluid being analyzed reach the analyzer 3, the latter produces electric signals transmitted to the display 9.

Fluid is supplied from the funnel 1 to the analyzer 3 by gravity; pure compressed air may also be used for the purpose, especially in the case of highly viscous fluid. For instance, the aforementioned U.S. Pat. No. 3,669,542 describes the feeding of air into a container to enhance flow of a liquid being analyzed.

All the particles accumulated in the portion 5 of the channel 2 may be washed away simultaneously, with some of these particles forming unstable aggregates. From the horizontal portion 5, such aggregates proceed to the vertical portion 6 which gradually expands in the zone 7 and gradually narrows down in the zone 8. Upon reaching the zone 7, such aggregates disintegrate because of the eddying, and the particles are uniformly distributed over the flow of fluid being analyzed. As a result, the data obtained by the apparatus 4 is highly reliable.

What is claimed is:

1. A device for introducing samples into an analyzer of an apparatus for granulometric analysis of particles contained in fluids, comprising: a funnel having an inlet and an outlet; and wall means for defining a channel for establishing communication between said funnel and the apparatus, said channel having an upstream end connected to said outlet of said funnel and a downstream end adapted to communicate with a supply channel of said analyzer, said channel having a horizontal portion, disposed immediately downstream of said funnel, said horizontal portion having a length sufficient to allow escape of entrapped gas from fluids contained therein and to collect and retain particles settling from fluids during escape of the gas, and said channel having a vertical portion disposed immediately downstream of said horizontal portion for agitating the fluids, said vertical portion having a diameter which first gradually increases from an initial diameter and then gradually reduces to approximately its initial diameter.

2. A device according to claim 1, wherein the length of said horizontal portion is between 3 and 5 times as long as the diameter of said horizonal portion, and wherein the maximum diameter of said vertical portion is between 4 and 6 times larger than the initial diameter.

3. A device for introducing liquid samples having particles suspended therein into an analyzer, the device comprising:
   wall means for defining a liquid holding chamber having an inlet for receiving liquid and an outlet; and
   channel means having walls for defining a channel extending from the outlet of said wall means to an inlet of the analyzer, said channel means having a first generally horizontal portion disposed adjacent said outlet of said wall means to receive liquid and to allow escape of gas entrapped in the liquid and to retain particles settling from the liquid during escape of the gas, and a second generally vertical portion disposed downstream of said first portion to receive and to agitate the liquid and settled particles before the liquid enters the inlet of the analyzer, said second portion having a diverging portion with an upstream inlet and a downstream outlet, and a converging portion having an inlet facing the outlet of the diverging portion and an outlet connectable to the inlet of the analyzer.

4. The device of claim 3, wherein the channel has a predetermined diameter, and wherein the length of said horizontal portion is at least 3 and not more than 5 times the predetermined diameter.

5. The device of claim 3 or 4, wherein said inlet of said diverging portion has a predetermined diameter, and wherein the combined length of said diverging and said converging portions is at least 4 and not more than 6 times the diameter of said diverging portion inlet.

* * * * *